United States Patent
Huttner

(10) Patent No.: US 7,213,597 B2
(45) Date of Patent: May 8, 2007

(54) DISPOSABLE LOW-MELT THERMOPLASTIC MASK INCORPORATING AN INTEGRAL LOCKING MECHANISM FOR ATTACHMENT TO PATIENT RESTRAINT BOARDS

(75) Inventor: James J. Huttner, Sylvania, OH (US)

(73) Assignee: Bionix Development Corporation, Toledo, OH (US)

( * ) Notice: Subject to any disclaimer, the term of this patent is extended or adjusted under 35 U.S.C. 154(b) by 188 days.

(21) Appl. No.: 10/924,547

(22) Filed: Aug. 24, 2004

(65) Prior Publication Data

US 2005/0045187 A1    Mar. 3, 2005

Related U.S. Application Data

(60) Provisional application No. 60/497,618, filed on Aug. 25, 2003.

(51) Int. Cl.
*A61B 19/00* (2006.01)
(52) U.S. Cl. .......................... 128/869; 128/846; 24/458
(58) Field of Classification Search ................. 24/457, 24/458; 411/45, 46, 47, 48; 128/857, 869, 128/845, 846, 870
See application file for complete search history.

(56) References Cited

U.S. PATENT DOCUMENTS

| | | | | |
|---|---|---|---|---|
| 5,759,002 A | * | 6/1998 | Essenberg | 411/45 |
| 5,775,337 A | * | 7/1998 | Hauger et al. | 128/869 |
| 6,045,309 A | * | 4/2000 | LeVey | 411/45 |
| 6,749,384 B1 | * | 6/2004 | Ellis | 411/45 |

* cited by examiner

*Primary Examiner*—Patricia Bianco
*Assistant Examiner*—Camtu Nguyen
(74) *Attorney, Agent, or Firm*—Marshall & Melborn, LLC

(57) ABSTRACT

A disposable mask system for positioning a patient relative to a patient restraint board during radiation therapy includes a piece of low-melt thermoplastic material affixed to a rigid, non-thermoplastic frame. A lock-down mechanism is integrally incorporated into the rigid, non-thermoplastic frame, such that a manipulable portion of the lock-down mechanism extends upward from the surface of the rigid frame so that it is accessible by the user. An engagement member extends downward from the underside of the rigid frame such that it can engage corresponding holes in a patient restraint board, such that when the rigid frame is pushed down so that its engagement members fully engage the corresponding holes of the patient restraint board, then the thermoplastic mask system may by tightly secured to the patient restraint board by activating the lock-down mechanism.

10 Claims, 10 Drawing Sheets

DISPOSABLE LOW-MELT THERMOPLASTIC MASK INCORPORATING AN INTEGRAL LOCKING MECHANISM FOR ATTACHMENT TO PATIENT RESTRAINT BOARDS

CROSS-REFERENCE TO RELATED APPLICATION

This application is claiming the benefit, under 35 U.S.C. § 119(e), of the provisional application filed Aug. 25, 2003 under 35 U.S.C. § 111(b), which was granted Ser. No. 60/497,618. This provisional application is hereby incorporated by reference in its entirety.

BACKGROUND OF THE INVENTION

Cancer treatment using external beam radiation therapy is a common and growing method of treatment for patients with many kinds of cancers. In almost all of these patients, cancerous tissue lies adjacent to healthy tissue, which often contains important organs, nerves, and other structures that can be exquisitely sensitive to radiation injury. Therefore, during the course of treatment great care must be taken to spare normal tissue and only irradiate the cancerous tissue.

The treatment process using external beam radiation therapy is complex and exacting. It almost always entails multiple treatments given over several weeks to complete the course of therapy. Because of this, the patient must be positioned and re-positioned accurately for each radiation therapy treatment to ensure that the proper radiation dose is delivered only to diseased tissue, and to spare the normal tissue as much as possible.

To this end, a number of devices have been developed to ensure the exact positioning of the patient. Many of these positioning devices rely on the use of a form-fitting low-melt thermoplastic "mask" of the patient's head, head and shoulders, or other body anatomy to hold the patient in exactly the same position time after time, thus ensuring that there is no patient movement during the treatment process.

The use of such devices has become commonplace in the industry. They are considered "disposable", i.e., intended for single patient use only, and are meant to be discarded after the patient completes their course of therapy. They are formed of an injection molded, non-thermoplastic frame bonded to the sheet of low-melt thermoplastic. The form-fitting mask is typically made by heating the low-melt thermoplastic in a water bath until the material becomes pliable. It is then removed from the water bath, and then draped over the patient's face or torso and pressed to conform tightly to the patient's anatomy. As the material cools, it again becomes stiff and rigid, and thereby immobilizes the patient for his/her course of radiation therapy.

A common complaint with patients treated in this manner is that the set-up time, i.e. the time required to position the patient accurately for treatment, is time consuming and thus costly. It is therefore desirable to speed up and simplify the set-up process to increase treatment accuracy and patient throughput.

All current disposable low-melt thermoplastic masks must be locked down to the patent restraint system being used via some form of clamping mechanism. Current devices utilize screw-down clamps and other similar devices to affix the mask to the restraint board. Some other systems use a non-disposable holder into which the disposable thermoplastic mask is placed and secured, either by screw-clamps or "snap fit" mechanisms; this holder is then clamped to the restraint board using mechanisms similar to those described above.

In all of these cases the thermoplastic mask itself does not possess any mechanism that allows it to be easily and securely affixed to the treatment board. All must be attached to the treatment board in a laborious and time-consuming fashion, requiring several radiation technologists (those folks responsible for patient setup) be involved in the set-up process.

BRIEF SUMMARY OF THE INVENTION

This invention relates to an improvement over the standard head or head and shoulder low-melt thermoplastic mask that simplifies patient set-up, reduces set-up time, and provides for a more efficient treatment process.

The invention incorporates a unique locking system directly into the rigid frame surrounding the piece of low-melt thermoplastic. This allows the frame to be locked down onto the patient restraint device directly and easily, eliminating the need for cumbersome clamping mechanisms which can prolong set-up times, frustrate techs, and may lead to treatment inaccuracy as the lock down mechanisms wear and shift with time and use. No other current disposable low-melt thermoplastic frames incorporate such a mechanism into its construction.

BRIEF DESCRIPTION OF THE DRAWINGS

The advantages of the invention will become readily apparent to those skilled in the art from the following detailed description of various embodiments when considered in the light of the accompanying drawings, in which.

DETAILED DESCRIPTION OF THE INVENTION

Figure 1:
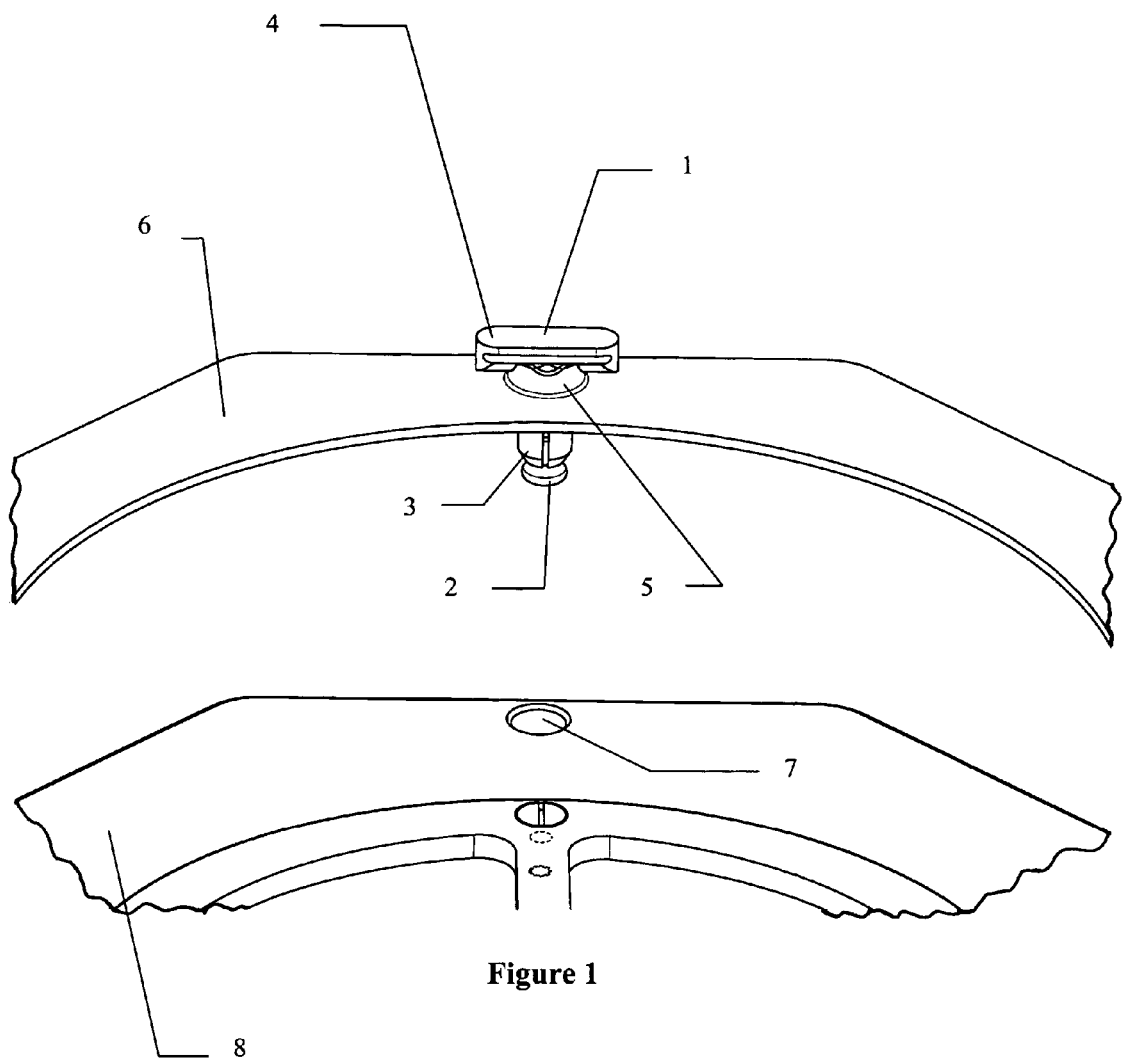
FIG. 1 is a partial, isometric view of the invention in its "unlocked" position and positioned above a patient restraint board.

It is to be understood that the specific devices and processes illustrated in the attached drawings and described in the following description are simply exemplary embodiments of the inventive concepts defined in the appended claims. Hence, specific dimensions and other physical characteristics relating to the embodiments disclosed herein should not be considered as limiting, unless the claims expressly state otherwise.

The invention relates to a thermoplastic mask system comprised of a sheet of die-cut low-melt thermoplastic bonded or glued or otherwise secured to a rigid, non-thermoplastic frame, usually in a U-shape or other configuration. The low-melt thermoplastic material has specific properties; i.e., when it reaches a specific temperature the thermoplastic softens and becomes extremely pliable, allowing the material to be stretched over a patient's head or other body part, conforming tightly to the patient's anatomy. As it cools, the thermoplastic becomes rigid again, and holds the shape to which it has been conformed. In this way, the thermoplastic forms a mask that tightly conforms to the patient's unique anatomical shape. The rigid, non-thermoplastic frame serves as a handle to allow the radiation technologist to manipulate the pliable, warm thermoplastic, and helps the technologist to stretch the warm pliable material over the patient's anatomy. The thermoplastic mask, once formed, cannot be easily re-formed to fit another patient. Thus, it is intended for single patient use, and is meant to be disposable after completing the patient's course of therapy.

The current invention incorporates a simple locking mechanism directly into the frame of a thermoplastic mask, making the device able to be locked-down to a patient restraint board without the use of accessory clamping mechanisms. This modification to existing technology facilitates the use of the thermoplastic mask by enhancing both the speed and accuracy by which a thermoplastic mask of a patient's anatomy may be made. In current designs, two or more radiation technologists are required to form the mask, one to push the pliable warm thermoplastic over the patient's face or torso, and another to position and tighten the clamping mechanism. Incorporating the locking mechanism directly into the frame of the thermoplastic mask makes it possible for a single radiation technologist to form the frame over the patient and lock it securely to the restraint board until it cools to rigidity.

The locking mechanism may take several forms. In the preferred embodiment, the locking mechanism includes a rotating cam-like mechanism that functions to draw closer or extend a locking pin closer-to or further-from the rigid, non-thermoplastic frame. The locking pin has an expander at its tip that engages a split expandable member on the underside of the frame. When the locking mechanism is rotated from the "open" to "locked" position, the locking pin is pulled tighter to the frame forcing the expander at its tip to engage and expand the expandable member on the underside of the frame.

In use, the warm, pliable thermoplastic is forced down over the patient, conforming to his/her anatomy. The locking mechanism is in the "open" position. The expander members on the underside of the rigid non-thermoplastic frame mate with corresponding holes in the restraint board that have a reverse frusto-conical shape to them. When the thermoplastic is fully conformed to the patient's anatomy and the expander members on the underside of the rigid frame are fully engaged into the corresponding holes in the restraint board, the locking cam is rotated to the "locked" position. This forces the expandable members to expand and tightly engage the restraint board, holding the finished thermoplastic mask securely in place.

Other forms of integral locking mechanisms are possible, including a variation of the preferred embodiment utilizing a panel rivet-like mechanism to expand the expandable member on the underside of the rigid frame. Still other forms may be envisioned using other cam-mechanisms and other means of expanding the expandable member. Still other embodiments may use a "lock and key" mechanism utilizing mating shapes of the hole in the restraint board and the member extending from the underside of the thermoplastic mask frame. Still other embodiments may utilize spring-loaded or similar mechanisms to engage suitably designed posts or similar members extending upward from the restraint board.

Other mechanisms may also be envisioned which meet the intent of incorporating the lock-down mechanism directly into the rigid frame of a disposable thermoplastic mask system. One such example is a latching mechanism utilizing a locking means extending downward from the underside of the rigid frame of the thermoplastic mask that mates with an undercut in the patient restraint board, such that when the rigid frame is pushed down onto the patient restraint board a ridge on the locking member engages the undercut in the restraint board in a secure manner, securing the thermoplastic mask system to the patient restraint board. A release mechanism is provided by a member extending upward from the rigid frame such that when the user squeezes or laterally moves the release member the locking means is levered laterally, releasing the engagement of the locking means and the undercut in the patient restraint board.

Referring now to the drawings, FIG. 1 shows an isometric view of the current invention in its "unlocked" position. In its preferred embodiment, the locking mechanism comprises a rotating cam-like mechanism that functions to draw closer or extend a locking pin closer-to or further-from the rigid, non-thermoplastic frame 6. The locking pin 1 has an expander at its tip 2 that engages a split expandable member 3 on the underside of the frame 6. A notched collar 5 and the split expandable member 3 are both integral parts of the frame 6. A plurality of these locking mechanisms are arrayed about the periphery of the frame 6 in sufficient number so as to securely lock the frame 6 to the patient restraint board 8 when the locking mechanism has been engaged.

When the locking pin is rotated from the "unlocked" to "locked" position, the cross-piece 4 at the top of the locking pin 1 engages the notched collar 5 on the top surface of the frame 6. This produces a cam-like action on the cross-piece that forces the locking pin upwards, causing the locking pin 1 to be pulled tighter to the frame 6. This in turn forces the expander at its tip 2 to engage and expand the expandable member 3 on the underside of the frame 6. A portion of the patient restraint board 8 with its corresponding hole 7 that mates to the locking pin 1 is also shown in FIG. 1.

Figure 2:
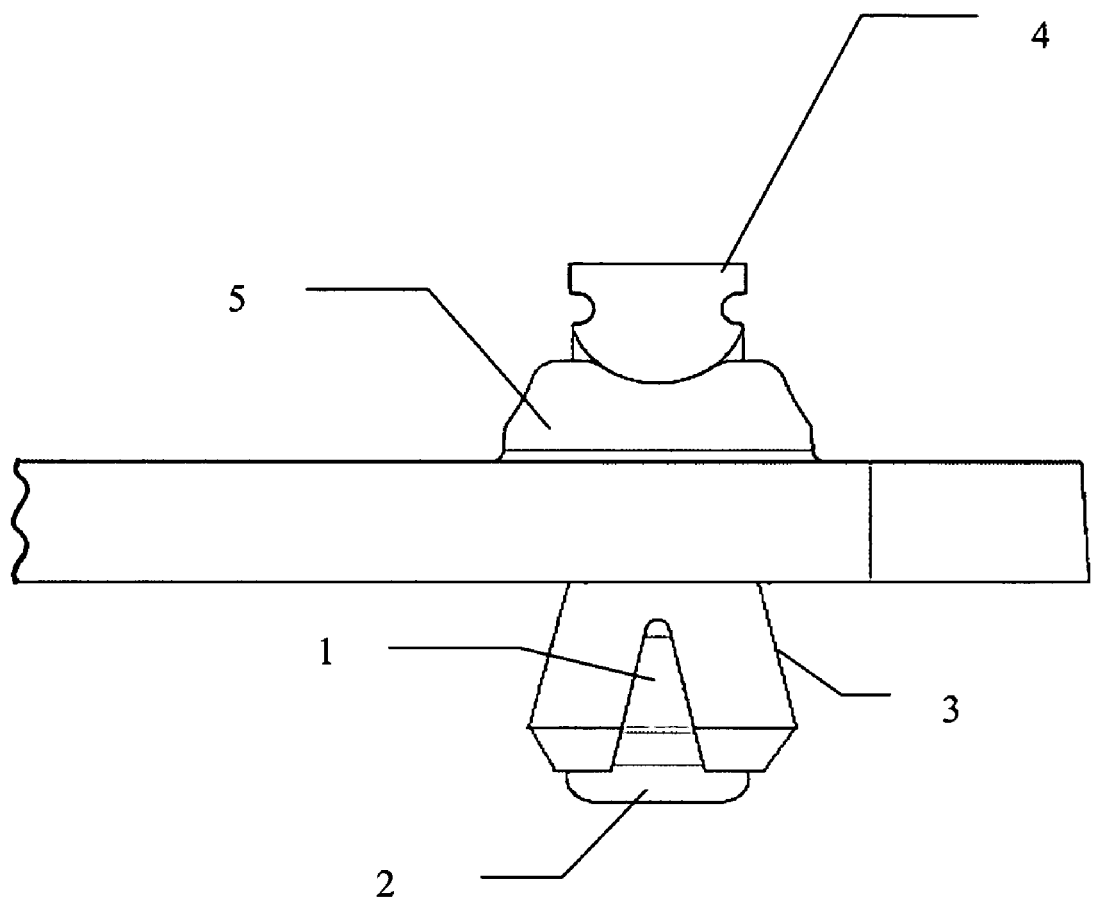
FIG. 2 is an enlarged side view of a portion of the invention illustrated in FIG. 1 in its "locked" position.

FIG. 2 illustrates in the invention in its "locked" position. In this view, the cross-piece 4 has been rotated 90 degrees, engaging the notched collar 5 as described, with the resulting cam-like action forcing the locking pin 1 upwards. In this figure, the expander at the tip of the locking pin 2 is shown as having engaged and expanded the expandable member 3 on the underside of the frame 6. The expanded expandable member on the underside of the frame is shown having engaged the corresponding hole in the patient restraint board, thereby locking the device securely to the patient restraint board.

Figure 3:
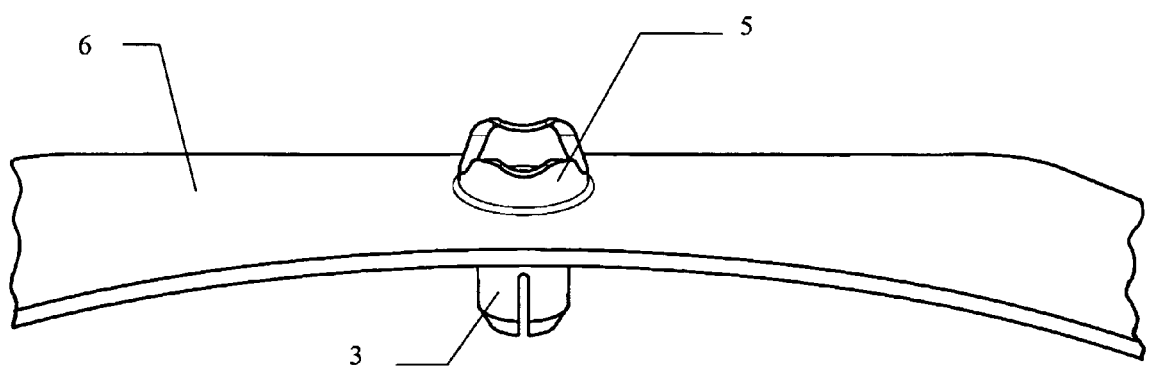
FIG. 3 is a top isometric view of the invention without a locking pin in place.

In the preferred embodiment illustrated in FIG. 3, the notched collar 5 is clearly depicted and is seen to be an integral part of the frame 6. The expandable member 3 is shown on the underside of the frame, and is also an integral part of the frame 6.

Figure 4:
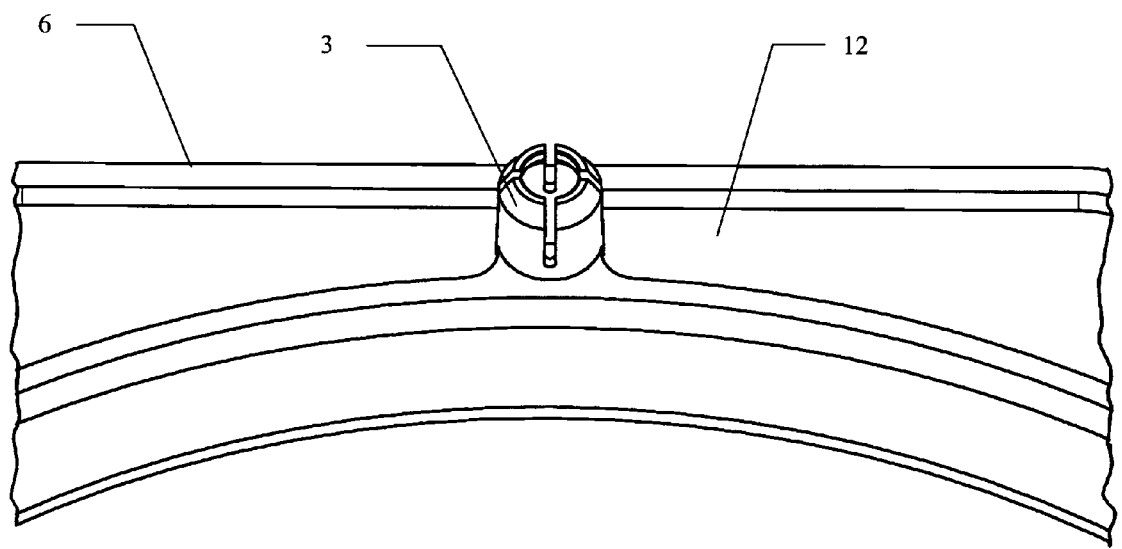
FIG. 4 is a bottom isometric view of the invention without the locking pin in place.

The underside of the frame 6, best seen in FIG. 4, is shown having a "shelled-out" structure 12 that decreases the radiation attenuation of the frame. The expandable member 3 is also shown in FIG. 4 as an integral part of the underside of the frame 6.

Figure 5:
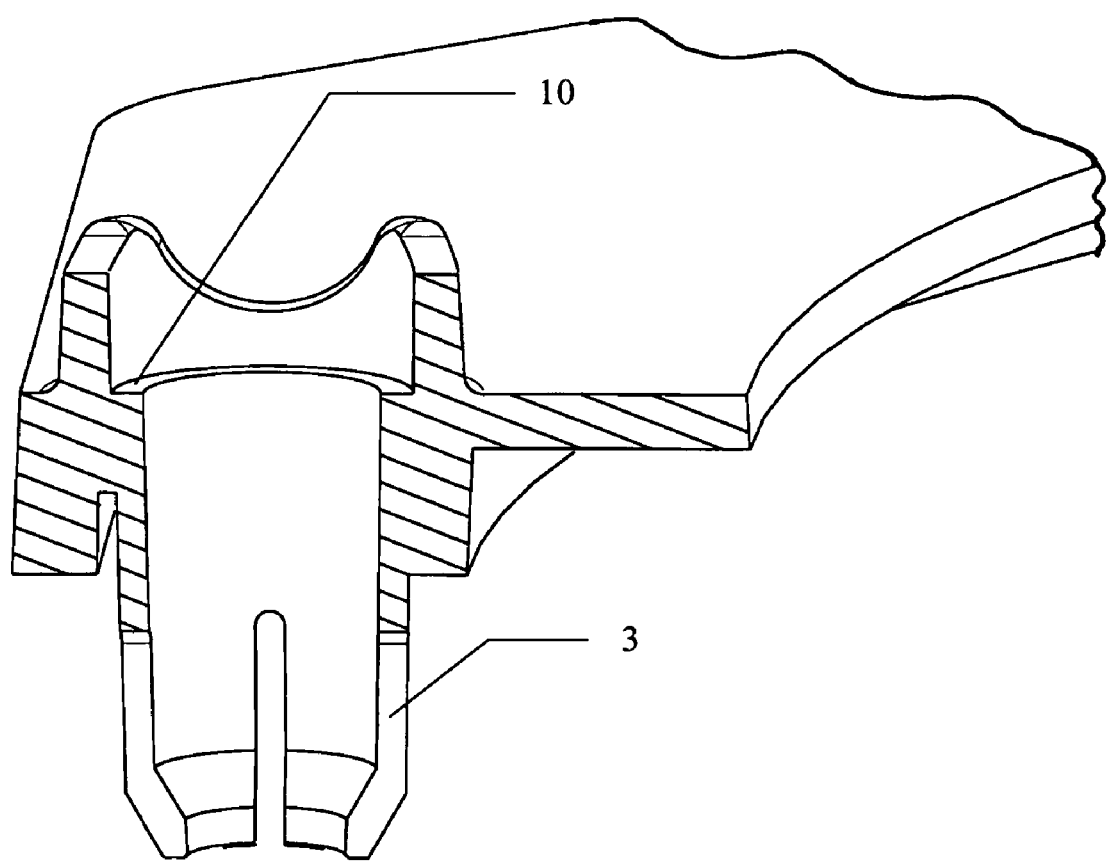
FIG. 5 is a cut-away isometric view of a portion of the invention without the locking pin in place.

FIG. 5 provides a clear view of the frame without the locking pin in place. A lip 10 is preferably formed in the interior of the expandable member 3. When inserted into the locking mechanism and the device is in the "unlocked" position, the expander tip extends beyond the tip of the expandable member. When the device is in the "locked" position, the expander tip is pulled upward and seats on the face of the lip 10, forcing the expandable member to flare outward and "locking" or selectively securing the device to the patient restraint board 8.

Figure 6:
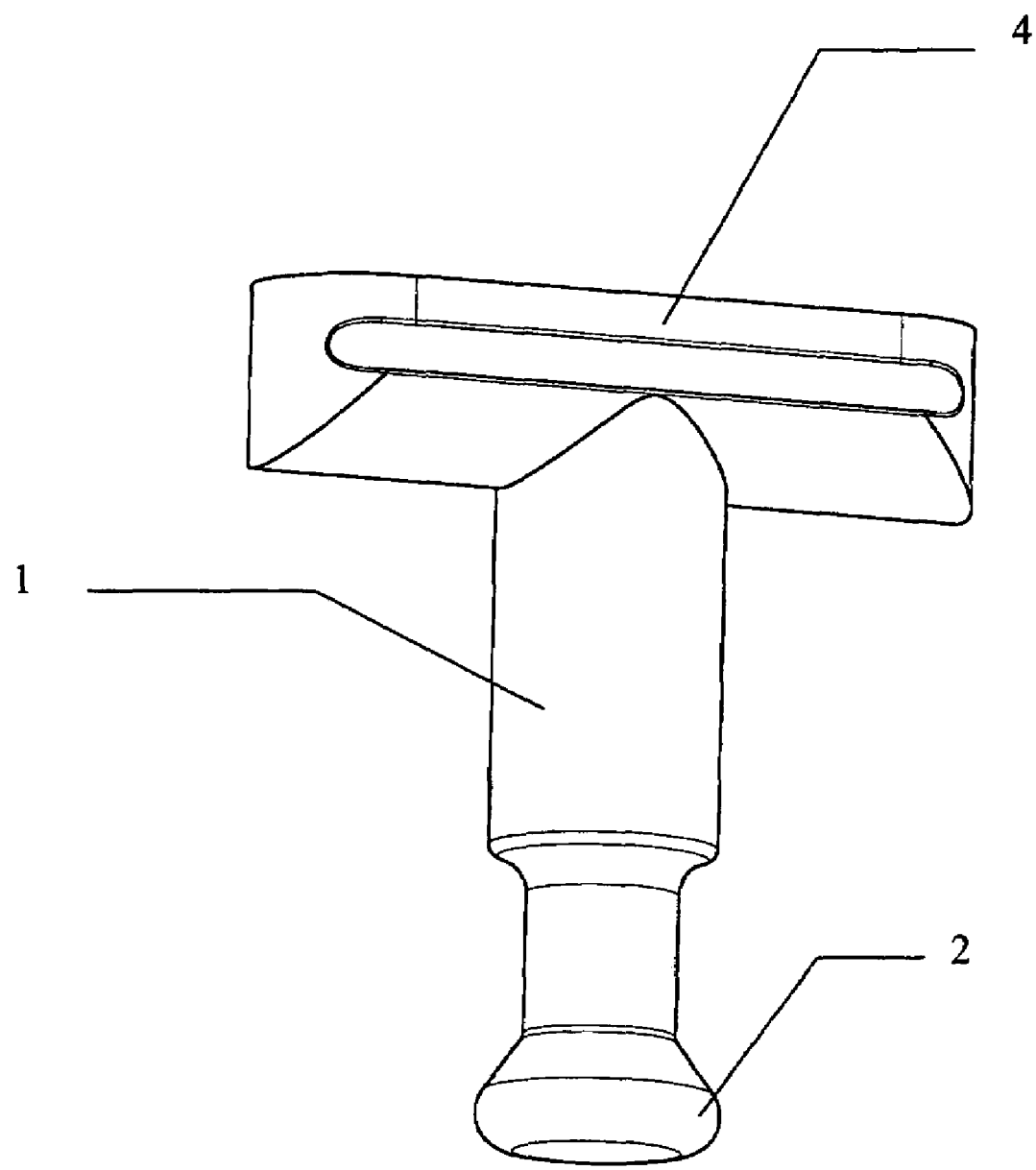
FIG. 6 is an isometric view of the locking pin only.

FIG. 6 shows the locking pin 1 only. In its preferred embodiment, the locking pin 1 has a T-shaped configuration, with the cross-piece 4 at the top and the expander tip 2 at the bottom. In use, the locking pin 1 is mated to the locking mechanism by inserting it into the notched collar and pushing until it seats in the recess in the inside of the expandable member. Alternate embodiments are possible that include modifications in design of the cross-piece and the expander tip.

Figure 7:
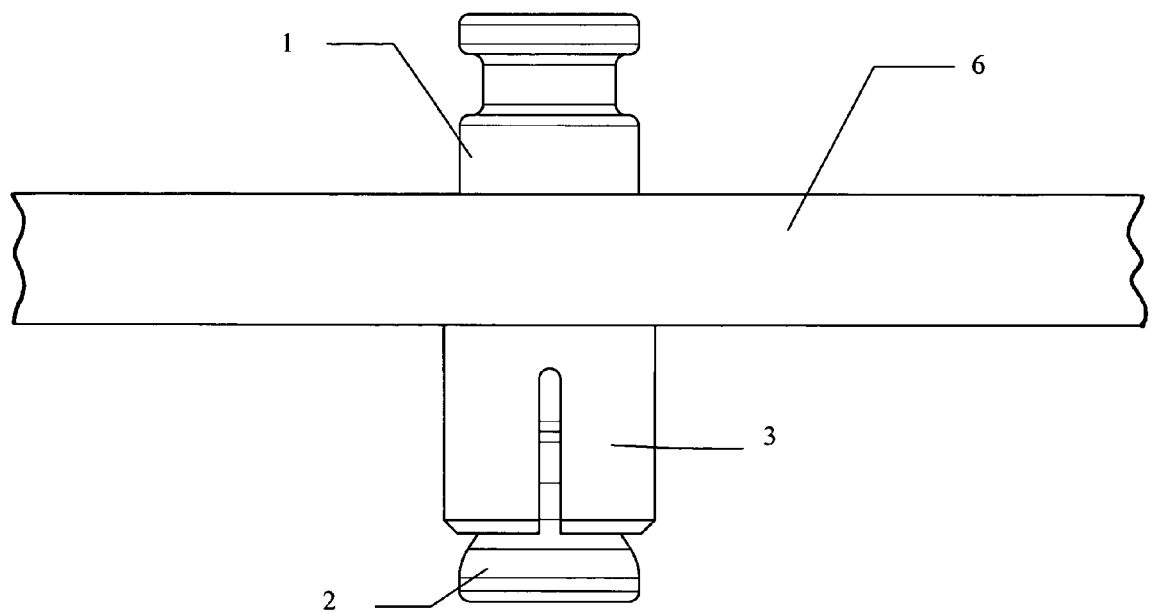
FIG. 7 is a side view of an alternative embodiment of the locking mechanism in accordance of the invention.

An alternate embodiment of the locking mechanism is shown in FIG. 7. Again seen is the locking pin 1', shown in an alternate configuration. The expandable member 3 is seen as before, and is an integral part of the frame 6, as before. The notched collar is not depicted because it has no function in this embodiment, and is therefore omitted. In this embodiment, the device functions in the same fashion as a panel rivet. When the locking pin is in its "unlocked" position, the expander tip seats within the recess in the expandable member 3, as above. When the locking pin 1' is depressed, the expander tip 2' forces the expandable member to expand, thereby selectively locking the device to the patient restraint board.

Figure 8:
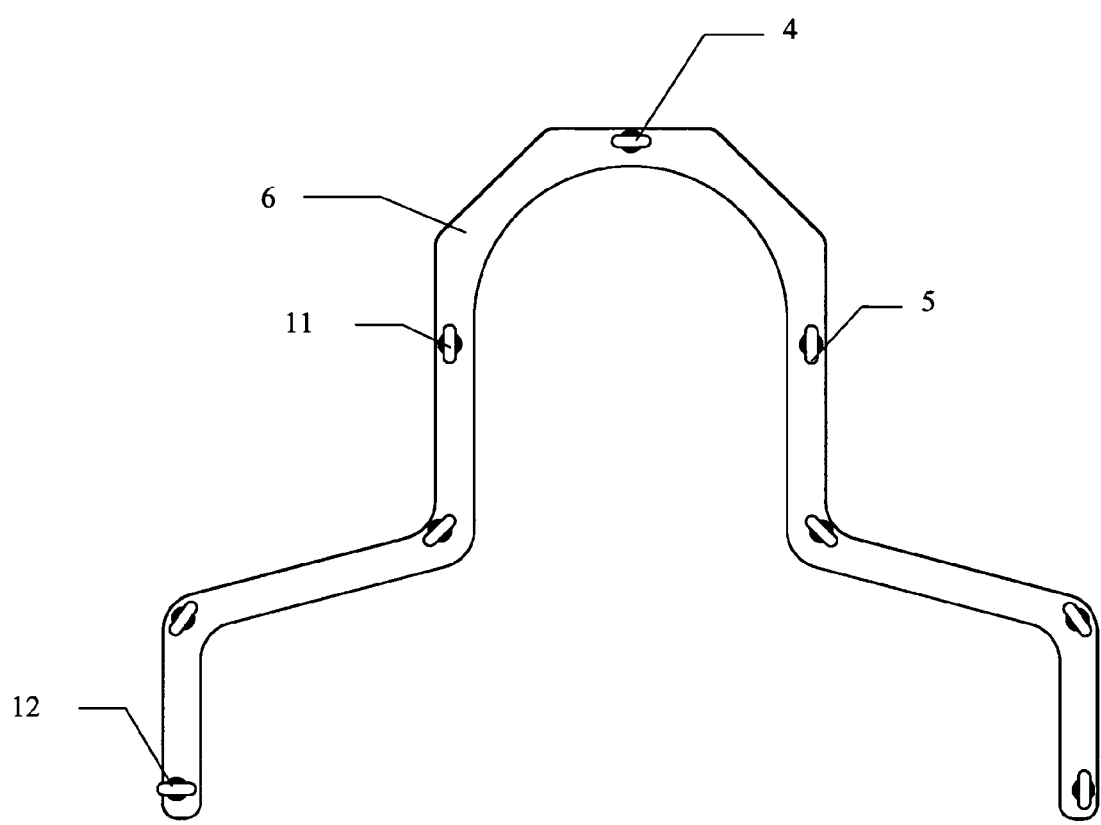
FIG. 8 is a top view of the entire rigid, non-thermoplastic frame in accordance with the invention.

FIG. 8 illustrates an entire rigid, non-thermoplastic frame 6. The outline is configured to match commercially available patient restraint boards. It is understood that this configuration may be changed to match other commercially available boards. In the preferred embodiment, a plurality of locking mechanisms are arrayed along the length of the frame 6 in sufficient number so as to securely lock the frame 6 to the patient restraint board when the locking mechanism has been engaged. In this figure, the locking mechanisms are shown in their assembled, ready-to-use form. The locking pin cross-pieces 4 can be seen resting in their respective notched collars 5. In this view, cross-pieces oriented parallel to the linear axis of the frame will be in the "unlocked" position (as shown at numeral 11), whereas cross-pieces oriented perpendicular to the linear axis of the frame will be in the "locked" position (as shown at numeral 12).

Figure 9:
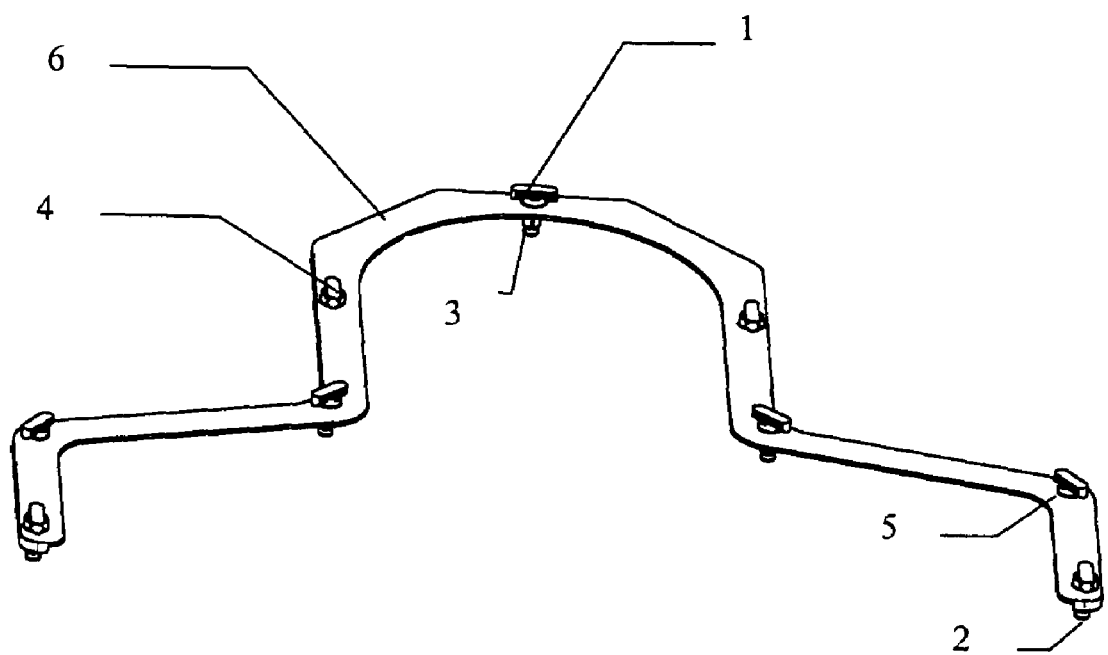
FIG. 9 is an isometric view of the entire rigid, non-thermoplastic frame shown in FIG. 8.

Referring to FIG. 9, the T-shape of the locking pin 1 is shown, again with the cross-piece 4 resting in the notched collar 5. Also in this view is seen the expandable member 3 on the underside of the frame 6, with the expander tip 2 of the locking pin 1 visible. Again, some of the locking mechanisms are shown in the "un-locked" position, and some are shown in the "locked" position.

Figure 10:
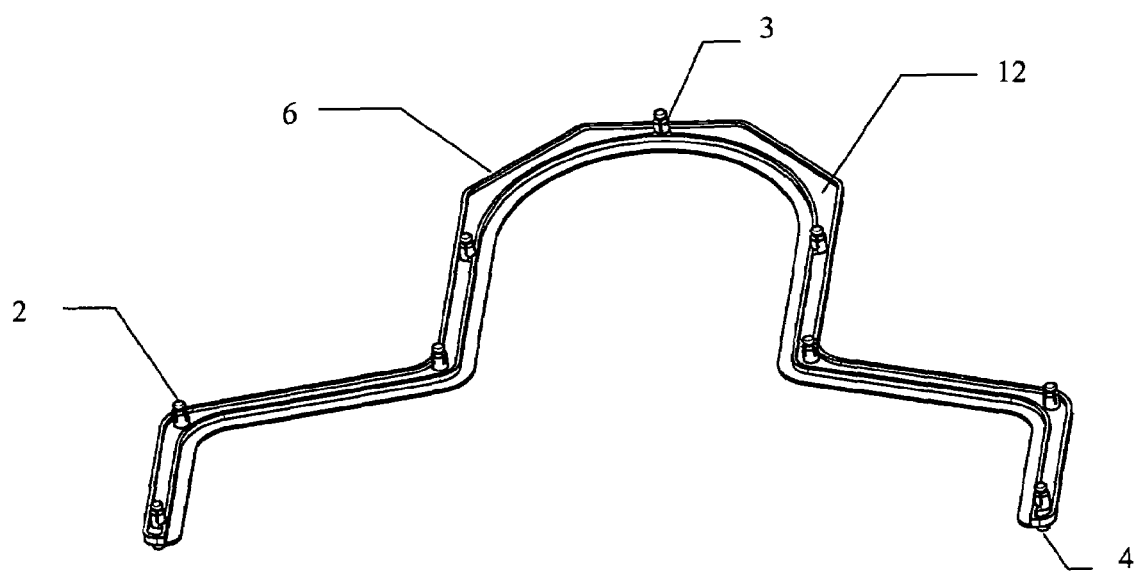
FIG. 10 shows an isometric view of the underside of the rigid, non-thermoplastic frame shown in FIG. 8.

From the underside of the rigid, non-thermoplastic frame 6 shown in FIG. 10, the "shelled-out" structure 12 of the frame is seen. The slotted expandable members 3 of the locking mechanisms are seen, and are an integral part of the frame. The expander tip 2 of the locking pin 1 can be seen protruding just past the expandable member 3. Again, the cross-pieces 4 of several locking pins are shown, some in the "locked" and some in their "unlocked" position.

In accordance with the provisions of the patent statutes, the invention has been described in what is considered to represent its preferred embodiments. However, it should be noted that the invention could be practiced otherwise than as specifically illustrated and described without departing from its spirit or scope. As an example, it will be appreciated that, in those embodiments in which the apparatus includes a plurality of projections, the size and shape of the projections may vary considerably.

What is claimed is:

1. A disposable mask system comprised of a piece of low-melt thermoplastic material affixed to a rigid, non-thermoplastic frame, with a lock-down mechanism integrally incorporated into the rigid, non-thermoplastic frame, such that a manipulable portion of the lock-down mechanism extends upward from the surface of the rigid frame so that it is accessible by the user, and where an engagement member formed integrally with the rigid frame extends downward from the underside of the rigid frame such that it can engage corresponding holes in a patient restraint board, such that when the rigid frame is pushed down so that its engagement members fully engage the corresponding holes of the patient restraint board, then the thermoplastic mask system may be tightly secured to the patient restraint board by activating the lock-down mechanism.

2. The device of claim 1, wherein the lock-down mechanism is comprised of a rotating cam-like mechanism that functions to draw closer or extend a locking pin closer-to or further-from the rigid, non-thermoplastic frame, and the locking pin has an expander that engages a split expandable member on the underside of the frame, wherein when the locking mechanism is rotated from the open to locked position, the locking pin is pulled tighter to the frame forcing the expander to engage and expand the expandable member on the underside of the frame.

3. The device of claim 2, wherein the corresponding holes of the patient restraint board have a reverse frusto-conical shape to them, such that when the thermoplastic is fully conformed to the patient's anatomy and the expander members on the underside of the rigid frame are fully engaged into the corresponding holes in the restraint board, the locking cam is rotated to the "locked" position, forcing the expandable members to expand and tightly engage the restraint board, holding the finished thermoplastic mask securely in place.

4. The device of claim 1, wherein the lock-down mechanism is comprised of a panel rivet design, such that depressing the head of a plurality of panel rivets extending upward from the surface of the rigid frame forces expansion of corresponding expandable members on the underside of the rigid frame, and when the expandable members on the underside of the rigid frame are fully engaged into the corresponding holes in the restraint board, then the expansion of the expandable members on the underside of the rigid frame securely engages the finished thermoplastic mask in place on the patient restraint board.

5. A disposable mask system for securing a mask formed of a piece of low-melt thermoplastic material to a patient restraint board, comprising a rigid, non-thermoplastic frame and a lock-down mechanism, the lock-down mechanism comprising a plurality of engagement members integrally formed with and extending downward from the underside of the frame and being adapted to engage corresponding holes in the patient restraint board and a plurality of lock-down activating members, each activating member cooperating with a corresponding one of the engagement members and having a manipulable portion extending upward from the surface of the rigid frame so that it is accessible by a user, wherein when the rigid frame is pushed down so that the engagement members fully engage the corresponding holes of a patient restraint board, then the thermoplastic mask system may be selectively and tightly secured to the patient restraint board by manipulation of the activating members of the lock-down mechanism.

6. The mask system of claim 5, wherein the lock-down mechanism is comprised of a rotating cam-like mechanism in which each of the engagement members is comprised of a split expandable member and each of the activating members is comprised of a locking pin, wherein rotation of a locking pin in a first direction causes the expander of that locking pin to engage and expand the corresponding split expandable member, thereby drawing the locking pin and rigid frame closer to the patient restraint board.

7. The mask system of claim 6, further comprising a patient restraint board, wherein the corresponding holes of the patient restraint board have a reverse frusto-conical shape to them, such that when the thermoplastic mask is fully conformed to a patient's anatomy and the expandable members on the underside of the rigid frame are fully engaged into the corresponding holes in the restraint board, the locking pins are rotated to force the expandable members to expand and tightly engage the restraint board, holding the frame and finished thermoplastic mask securely in place.

8. The mask system of claim 6, further comprising a plurality of notched collars integrally formed with and extending upwardly from the rigid frame so as to be in alignment with a corresponding one of the engagement members, each of the notched collars defining a cam surface in engagement with a cam follower surface formed on a corresponding one of the locking pins.

9. The mask system of claim 5, wherein each of the engagement members is comprised of a split expandable member and each of the activating members is comprised of a panel rivet, such that depressing each panel rivet forces expansion of a corresponding expandable member on the underside of the rigid frame, and when the expandable members on the underside of the rigid frame are fully engaged into the corresponding holes in a patient restraint board, then the expansion of the expandable members on the underside of the rigid frame securely engages the finished thermoplastic mask in place on the patient restraint board.

10. The mask system of claim 5 secured to a patient restraint board.

* * * * *